United States Patent
Elings et al.

(10) Patent No.: US 10,226,062 B2
(45) Date of Patent: Mar. 12, 2019

(54) ORGANIC COMPOUNDS

(71) Applicant: Givaudan, S.A., Vernier (CH)

(72) Inventors: Jacob Antonius Elings, Huizen (NL); Stefan Michael Furrer, Cincinnati, OH (US); Abdelmajid Kaouas, Utrecht (NL); Cornelis Winkel, Bussum (NL)

(73) Assignee: Givaudan SA, Vernier (CH)

( * ) Notice: Subject to any disclaimer, the term of this patent is extended or adjusted under 35 U.S.C. 154(b) by 348 days.

(21) Appl. No.: 15/037,871

(22) PCT Filed: Dec. 4, 2014

(86) PCT No.: PCT/EP2014/076639
§ 371 (c)(1),
(2) Date: May 19, 2016

(87) PCT Pub. No.: WO2015/082645
PCT Pub. Date: Jun. 11, 2015

(65) Prior Publication Data
US 2016/0295903 A1    Oct. 13, 2016

Related U.S. Application Data

(60) Provisional application No. 61/912,183, filed on Dec. 5, 2013.

(51) Int. Cl.
| | | |
|---|---|---|
| *A23L 27/20* | (2016.01) | |
| *C07C 217/58* | (2006.01) | |
| *A23L 27/00* | (2016.01) | |
| *C07C 217/64* | (2006.01) | |
| *C07D 317/58* | (2006.01) | |

(52) U.S. Cl.
CPC ............ *A23L 27/88* (2016.08); *A23L 27/204* (2016.08); *A23L 27/2052* (2016.08); *C07C 217/58* (2013.01); *C07C 217/64* (2013.01); *C07D 317/58* (2013.01)

(58) Field of Classification Search
CPC .... A23L 27/88; A23L 27/204; A23L 27/2052; C07D 317/58; C07C 217/64; C07C 217/58
See application file for complete search history.

(56) References Cited

U.S. PATENT DOCUMENTS

| | | | | |
|---|---|---|---|---|
| 2,820,739 | A * | 1/1958 | Brown | A61K 31/135 514/452 |
| 2006/0159818 | A1 | 7/2006 | Kunieda | |
| 2007/0178123 | A1* | 8/2007 | Levenson | A61K 9/0053 424/400 |
| 2012/0226047 | A1 | 9/2012 | Shigemura et al. | |
| 2012/0308703 | A1 | 12/2012 | Ley et al. | |
| 2013/0266708 | A1 | 10/2013 | Shigemura et al. | |
| 2014/0004243 | A1 | 1/2014 | Tahara et al. | |
| 2014/0295045 | A1 | 10/2014 | Wang et al. | |

FOREIGN PATENT DOCUMENTS

| | | |
|---|---|---|
| CN | 102697766 | 10/2012 |
| EP | 1 291 342 A1 | 3/2003 |
| EP | 1 312 268 A1 | 5/2003 |
| EP | 1 642 886 A2 | 4/2006 |
| EP | 1 649 759 A1 | 4/2006 |
| EP | 2 529 632 A1 | 12/2012 |
| JP | 09030960 A | 2/1997 |
| KR | 1020130070371 A | 12/2014 |
| WO | WO 00/76493 A1 | 12/2000 |
| WO | WO 03/088768 A1 | 10/2003 |
| WO | WO 2005/015158 A2 | 2/2005 |
| WO | WO 2006/003107 A1 | 1/2006 |
| WO | WO 2006/014507 A2 | 2/2006 |
| WO | WO 2011/004016 A1 | 1/2011 |
| WO | WO 2012/121273 A1 | 9/2012 |

OTHER PUBLICATIONS

Yamato, M., Sato, K., Hashigaki, K., Ishikawa, T., Oki, M., Koyama, T. 1974. "Chemical Structure and Sweet Taste of Isocoumarins and Related Compounds." Chem. Pharm. Bull. vol. 22, pp. 475-476.*
Yamato, M., Sato, K.,Hashigaki, K., Ishikawa, T., Oki, M., Koyama, T. 1974. "Chemical Structure and Sweet Taste of Isocoumarins and Related Compounds. V." Yakugaku Zasshi. vol. 94, pp. 359-361.*
PCT/EP2014/076639—International Search Report, dated Feb. 13, 2015.
PCT/EP2014/076639—International Written Opinion, dated Feb. 13, 2015.
PCT/EP2014/076639—International Preliminary Report on Patentability, dated Jun. 7, 2016.
GB1401087.0—Great Britain Search Report, dated Aug. 11, 2014.
Devries, Vern, et al., "Potential Antiatherosclerotic Agents. 6. Hypocholesterolemic Trisubstituted Urea Analogs", Journal of Organic Chemistry, Oct. 1, 1989, pp. 2318-2325, vol. 32, No. 10.

(Continued)

*Primary Examiner* — Nikki H. Dees
(74) *Attorney, Agent, or Firm* — Curatolo Sidoti Co., L.P.A.; Joseph G. Curaloto, Esq.; Salvatore A. Sidoti, Esq.

(57) ABSTRACT

This disclosure relates to taste modifiers of formula (I)

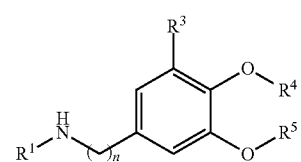

(I)

wherein,
n is 1, 2 or 3;
$R^1$ is selected from $C_1$-$C_5$ alkyl, $C_1$-$C_5$ hydroxyalkyl, $C_1$-$C_5$ dihydroxyalkyl and —CHYCOOH wherein Y is selected from $C_1$-$C_3$;
$R^3$ is hydrogen, hydroxy or $C_1$-$C_3$ alkoxy;
$R^4$ is hydrogen, or $C_1$-$C_3$ alkyl;
$R^5$ is selected from hydrogen, or $C_1$-$C_3$ alkyl;
or $R^4$ and $R^5$ form together a bivalent radical —$CH_2$—;
that are able to impart, enhance or modify salt or umami taste.

9 Claims, No Drawings

(56) References Cited

OTHER PUBLICATIONS

Kindler, Kari, et al., "Über neu und über verbesserte Wge zum Aufbau von pharmakologisch wichtigen Amien V", Archiv Der Pharmazie, 1932, p. 353-362, vol. 270, No. 471. German Only.
Luts, Heino, et al., "Neurodepressive Agents I", Journal of Pharamceutical Sciences, Mar. 1965, pp. 460-461, vol. 54.
Nyberg, Wayne H., et al., "3-piperonylsydnone. A New Type of Antimalarial Agent", Journal of Medicinal Chemistry, Jul. 1965, pp. 531-533, vol. 8, No. 4.
Orito, Kazuhiko, et al., "Pd(OAc)2-catalyzed Carbonylation of Amines", The Journal of Organic Chemistry, Aug. 4, 2006, pp. 5951-5958, vol. 71, No. 16.
Stefko, P.L, et al, "Experimental Investigation of Nine Antitussive Drugs", Journal of Pharaceutical Sciences, 1961, pp. 216-221, vol. 50, No. 3.
Yamato, et al., "Chemical Structure and sweet Taste of Isocoumarins and Related Compounds", Chemical Senses and Flavor, Jan. 15, 1979, pp. 35-47, Vo . . . 4, No. 1.
Yu, Melvin J, et al., "Benzylamine Antioxidants: Relationship between Structure, Peroxyl Radical Scavenging, Lipid Peroxidation Inhibition, and Cytoprotection", Journal of Medicinal Chemistry, 1993, pp. 1262-1271, vol. 36, No. 9.

\* cited by examiner

ORGANIC COMPOUNDS

CROSS REFERENCE TO RELATED APPLICATIONS

This application is a national stage application of International Application No. PCT/EP2014/076639, filed 4 Dec. 2014, which claims priority from U.S. Provisional Patent Application No. 61/912,183, filed 5 Dec. 2013, which applications are incorporated herein by reference.

This invention relates to the discovery of taste modifiers, in particular taste modifiers that are able to impart, enhance or modify salt or umami taste in a comestible product such as a food or a beverage. The invention relates also to comestible products containing said modifiers.

It is common practice to add various naturally occurring and synthetic compounds to comestible (edible) foods, beverages to improve their taste. However, there remains in the art a need for new and improved flavoring agents. This is particularly true in the field of umami flavour modifiers. Currently, there are very few compounds identified that can be considered as substitutes for the flavour of monosodium glutamate (or "MSG"). Noteworthy are the naturally occurring nucleotide compounds inosine monophosphate (IMP) or guanosine monophosphate (GMP), but these compounds are costly to isolate and purify. New tastant compounds that would provide the savory flavor of MSG itself, so as to substitute for MSG as a savory tastant, or new compounds that enhance the effectiveness of MSG so as to substitute for IMP or GMP as MSG enhancers, could be of very high value.

The sensitivity of chemical structure and the perception of taste is well known. MSG, as we know, is a highly potent umami tastant. Yet, the structurally related compound aspartic acid (one methylene radical removed from MSG) has hardly any umami taste at comparable concentrations.

The biology of salt sensation is an equally complex matter, making prediction of salt taste based on structure very unreliable. Salt taste is uniquely provided by sodium chloride (NaCl). All other salts lack at least some of the typical positive taste attributes of sodium chloride. Potassium chloride tastes somewhat salty but clearly more bitter. Sodium acetate or sodium gluconate have hardly any taste. Lead chloride is even tasting sweet.

There remains a need to provide compounds that are useful for imparting, modifying or enhancing an umami- and/or salt-taste to a comestible product.

Applicant has now found a new class of chemical structures based on aromatic secondary amines that impart, enhance or modify an umami- and/or salt-taste in a comestible product.

Accordingly, the invention applies in a first aspect to the use of an aromatic secondary amine for imparting, or modifying an umami- and/or salt-taste in a comestible, the amine is defined according to formula (I) or a comestibly acceptable salt thereof (for example, in the form of the hydrochloride or hydrobromide)

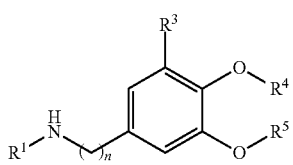

(I)

wherein,
n is 1, 2 or 3;
$R^1$ is selected from $C_1$-$C_5$ alkyl, $C_1$-$C_5$ hydroxyalkyl, $C_1$-$C_5$ dihydroxyalkyl (e.g. 1,3-dihydroxyprop-2-yl, 1,2-dihydroxyeth-2-yl, 1,5-dihydroxypent-3-yl, and methyldiol) and —CHYCOOH wherein Y is selected from $C_1$-$C_3$ alkyl (methyl, ethyl, propyl, iso-propyl);
$R^3$ is hydrogen, hydroxy or $C_1$-$C_3$ alkoxy (e.g. ethoxy);
$R^4$ is hydrogen, or $C_1$-$C_3$ alkyl (e.g. ethyl, isopropyl);
$R^5$ is selected from hydrogen, or $C_1$-$C_3$ alkyl (e.g. ethyl, isopropyl);
or $R^4$ and $R^5$ form together a bivalent radical —$CH_2$—.

A compound of formula (I) may contain chiral carbon atoms and, as such, can be employed in the present invention as a racemic mixture or in a resolved and isomerically pure form. The skilled person will immediately appreciate that the preparation of compounds of formula (I) can be achieved using straightforward synthetic procedures and readily available starting materials.

As used in relation to compounds of formula (I) unless otherwise indicated "alkyl" refers to linear or branched alkyl, for example, methyl, ethyl, propyl, iso-propyl, butyl, iso-butyl, tert-butyl, pentyl, pent-3-yl; "hydroxyalkyl" refers to linear and branched hydroxyalkyl, for example, hydroxymethyl, hydroxyethyl, hydroxyeth-2-yl, hydroxypropyl hydroxyprop-2-yl, hydroxyprop-3-yl, hydroxybutyl, hydroxybut-3-yl, hydroxybut-2-yl, 2-methyl hydroxyprop-3-yl, and 2-methyl hydroxypropyl.

Non-limiting examples are compounds of formula (I) wherein $R^4$ and $R^5$ form together a bivalent radical —$CH_2$—, and $R^3$ is hydrogen, and comestibly acceptable salts thereof (for example, in the form the hydrochloride).

Further, non-limiting examples are compounds of formula (I) wherein $R^4$ and $R^5$ form together a bivalent radical —$CH_2$—, and $R^1$ is selected from $C_1$-$C_5$ alkyl or $C_1$-$C_5$ hydroxyalkyl, and comestibly acceptable salts thereof (for example, in the form the hydrochloride).

Further non-limiting examples are compounds of formula (I) wherein $R^5$ is hydrogen and $R^4$ is methyl, ethyl or propyl, and comestibly acceptable salts thereof (for example, in the form the hydrochloride).

Further non-limiting examples are compounds of formula (I) wherein $R^4$ is hydrogen and $R^5$ is methyl, ethyl or propyl, and comestibly acceptable salts thereof (for example, in the form the hydrochloride).

As a further example of the invention's compound, one may cite N-piperonyl ethylamine (i.e. a compound of formula (I) wherein $R^1$ is ethyl, $R^3$ is hydrogen and $R^4$ and $R^5$ form together a bivalent radical —$CH_2$—), which imparted an umami- and salt-taste in comestible products.

Further, non-limiting examples are comestibly acceptable salt of the compound of formula (I) as hereinabove defined, for example, hydrochlorides, such as N-vanillyl ethylamine hydrochloride, or N-(2-hydroxyethyl) vanillylamine hydrochloride. Comestibly acceptable salts of the compounds of formula (I) are particular preferred when the compound as such is an oily product.

The aromatic secondary amines of the present invention may be obtained by reacting an aldehyde with an amine to form an imine with subsequent reduction of the imine to provide the desired aromatic amine of formula (I) as hereinabove defined. The reaction conditions, that is, the choice of solvent, temperature, pH and the like, appropriate for affecting the chemical syntheses described above are well known in the art and require no further elaboration here. Particular reaction conditions are set forth in the examples below.

The compounds of formula (I) may be used as the sole ingredient in a method of imparting, enhancing or modifying an umami and/salt taste in a comestible product, or they may be used as part of a flavour composition containing one or more additional flavour ingredients.

Accordingly, in another aspect, the invention is directed to a flavour composition comprising at least one compound of formula I as defined hereinabove.

The one or more said additional flavour ingredients may be selected from natural flavours, artificial flavours, spices, seasonings, and the like, synthetic flavour oils and flavouring aromatics and/or oils, oleoresins, essences, distillates, and extracts derived from plants, leaves, flowers, fruits, and so forth, Generally, any flavouring or food additive such as those described in Chemicals Used in Food Processing, publication 1274, pages 63-258, by the National Academy of Sciences, can be used. This publication is incorporated herein by reference.

Particular examples of other umami compounds that may be employed as additional flavour ingredients include the compounds described in UK patent application No. 0913804 and International Application No. PCT/EP2010/059916. Other non-limiting examples of umami flavour-conferring and -enhancing compounds include those described in EP 1642886, WO 2005/015158, EP 1312268, WO 2003/088768, EP 1291342 and WO 2006/003107, all of which references are incorporated herein by reference.

Compounds of formula (I) may be employed directly to the comestible or they may form a part of a flavour composition, which is subsequently admixed with the comestible product. In a particular embodiment they may be employed in amounts of about 0.001 to 100% (e.g. 0.1-10% by weight based on the flavor composition) of said flavour composition.

The compounds of formula (I) may be used in reduced salt/MSG flavour compositions, or in salt-/MSG-free flavour compositions, as well as those flavour compositions that contain salt/MSG in customary amounts. It is customary to employ MSG in such amounts that when a flavour composition is added to a comestible product, the MSG is present in amounts of between about 200 to 500 ppm. In reduced MSG comestible products, the amount of MSG is usually a lower amount in the range of about 100 to 200 ppm.

It is customary to employ salt (that is, sodium chloride) in such amounts such that when a flavour composition is added to a comestible product, the sodium chloride may be present in amounts of between about 0.8 and 2%. In reduced sodium chloride comestible products, the amount of sodium chloride is usually a lower amount in the range of about 0.4 to 0.8%.

The proportions of MSG, salt and compounds of formula (I), as well as any other flavour ingredients that might be desired will naturally depend on the desired flavour profile for any given formulation and the skilled person can easily determine the relevant proportions for any case by means of routine, non-inventive experimentation.

In another aspect, the invention is directed to a method of imparting saltiness to a comestible product, or enhancing or modifying the saltiness of a comestible product comprising the addition to said product, a compound of formula (I) or a flavour composition containing same, said comestible product containing salt (NaCl) in an amount of at least 0.3%.

In another aspect, the invention is directed to a method of imparting umami taste to a comestible product, or enhancing or modifying the umami taste of a comestible product comprising the addition to said product, a compound of formula (I) or a flavour composition containing same, said comestible product containing MSG in an amount of at least 50 ppm.

In a method of imparting, enhancing or modifying the umami and/or salt taste of a comestible product, an appropriate concentration in which to employ compounds of formula (I) will depend on the type of comestible product and the desired flavour intensity. For example, compounds according to formula (I) may be employed at a concentration of, for example, 1 to 2500 ppm, more particularly 1 to 100 ppm, still more particularly 5 to 50 ppm, based on weight of the comestible product.

The term "comestible product(s)" refers to any composition that is consumed for at least one of nourishment and pleasure, or that is placed in the mouth to achieve an effect before being discarded.

The comestible product may be in any physical form. Examples of comestible products wherein compounds according to the invention may be incorporated included by way of example the Wet Soup Category, the Dehydrated and Culinary Food Category, the Beverage Category, the Frozen Food Category, the Snack Food Category, and seasonings or seasoning blends.

"Wet Soup Category" means wet/liquid soups regardless of concentration or container, including frozen Soups. For the purpose of this definition soup(s) means a food prepared from meat, poultry, fish, vegetables, grains, fruit and other ingredients, cooked in a liquid which may include visible pieces of some or all of these ingredients. It may be clear as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consommé) to sauces (cream or cheese-based soups).

"Dehydrated and Culinary Food Category" means: (i) Cooking aid products such as powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology), (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

"Beverage Category" means beverages, beverage mixes and concentrates, including but not limited to, alcoholic and non-alcoholic ready to drink and dry powdered beverages. Other examples of foods and beverages wherein compounds according to the invention may be incorporated included by way of example carbonated and non-carbonated beverages, e.g., sodas, fruit or vegetable juices, alcoholic and non-alcoholic beverages, confectionary products, e.g., cakes, cookies, pies, candies, chewing gums, gelatins, ice creams, sorbets, puddings, jams, jellies, salad dressings, and other condiments, cereal, and other breakfast foods, canned fruits and fruit sauces and the like.

A person skilled in the art will appreciate that flavour formulations and comestible products of the present invention may contain additional ingredients, which may comprise various additives and excipients well known in the art, including anti-caking agents, anti-foaming agents, anti-oxidants, binders, colourants, diluents, disintegrants, emulsifiers, encapsulating agents or formulations, enzymes, fats, flavour-enhancers, flavouring agents, gums, lubricants, polysaccharides, preservatives, proteins, solubilisers, solvents, stabilisers, sugar-derivatives, surfactants, sweetening agents, vitamins, waxes, and the like. Solvents which may be used are known to those skilled in the art and include e.g. ethanol, ethylene glycol, propylene glycol, glycerine and triacetin. Encapsulants and gums include maltodextrin, gum arabic, alginates, gelatine, modified starch, and polysaccharides. Examples of additives, excipients, carriers, diluents or solvents for flavour or fragrance compounds may be found e.g. in "Perfume and Flavour Materials of Natural Origin", S. Arctander, Ed., Elizabeth, N.J., 1960; in "Perfume and Flavour Chemicals", S. Arctander, Ed., Vol. I & II, Allured Publishing Corporation, Carol Stream, USA, 1994; in "Flavourings", E. Ziegler and H. Ziegler (ed.), Wiley-VCH Weinheim, 1998, and "CTFA Cosmetic Ingredient Handbook", J. M. Nikitakis (ed.), 1st ed., The Cosmetic, Toiletry and Fragrance Association, Inc., Washington, 1988.

Any of the compounds of the present invention, additional flavour ingredients or any of the ingredients, additives or excipients may be formulated in an appropriate vehicle, e.g. they may be in encapsulated form, or bound in a matrix or the like, in order to achieve a desired technical effect such as to achieve stability or to effect controlled release.

There now follows a series of non-limiting examples that serve to illustrate the invention.

EXAMPLE 1.1: N-PIPERONYL METHYLAMINE

A 250 ml autoclave was charged with 100 ml of methylamine 2M in methanol (81 g, 200 mmol) and benzo[d][1,3]dioxole-5-carbaldehyde (10 g, 66.6 mmol) to give a colourless solution. The autoclave was closed and stirred at 35° C. for 3 hrs. Then 0.8 g of palladium 10% on carbon was added and then the autoclave was pressurized with 5 bar of hydrogen and stirred at ambient temperature until no more hydrogen was consumed. The reaction mixture was filtered to remove the catalyst. The filtrate was evaporated to furnish brownish oil. Kugelrohr distillation afforded 9.9 g of the title compound as a colourless oil (bp 190-200° C./12-10 mbar). Yield: 90%.

$^1$H-NMR in CDCl3: 2.42 (3H, s NH—CH3) 3.60-3.70 (2H, s, Ar—CH2-N), 5.85-5.95 (2H, s, O—CH2-O), 6.65-6.85 (3H, 2×m, 3× aromatic H).

EXAMPLE 1.2: N-PIPERONYL ETHYLAMINE

A 250 ml autoclave was charged with 100 ml of ethylamine 2M in methanol (81 g, 200 mmol) and benzo[d][1,3]dioxole-5-carbaldehyde (10 g, 66.6 mmol) to give a colourless solution. The autoclave was closed and stirred at 35° C. for 3 hrs. Then 0.8 g of palladium 10% on carbon was added and then the autoclave was pressurized with 5 bar of hydrogen and stirred at ambient temperature until no more hydrogen was consumed. The reaction mixture was filtered to remove the catalyst. The filtrate was evaporated to furnish the title compound as a colourless liquid (11.4 g; yield 95%). The product was pure according to GC and NMR analysis.

$^1$H-NMR in CDCl3: 1.05-1.15 (3H, m, NH—CH2-CH3), 2.60-2.70 (2H, m, —NH—CH2-CH3), 3.60-3.70 (2H, s, Ar—CH2-N), 5.85-5.95 (2H, s, O—CH2-O), 6.65-6.85 (3H, 2×m, 3× aromatic H).

EXAMPLE 1.3: N-PIPERONYL N-PROPYLAMINE

A 250 ml autoclave was charged with propan-1-amine (10 g, 169 mmol) and benzo[d][1,3]dioxole-5-carbaldehyde (5 g, 33.3 maid) in methanol (100 ml) to give a slightly yellow solution. The autoclave was closed and stirred at 35° C. for 3 hrs. Then 1 g of palladium 10% on carbon was added and then the autoclave was pressurized with 5 bar of hydrogen and stirred at ambient temperature until no more hydrogen was consumed. The reaction mixture was filtered to remove the catalyst. The filtrate was evaporated to yield the title compound as a colourless liquid (6.2 g; yield 96%). The product was pure according to NMR analysis.

$^1$H-NMR in CDCl3: 0.80-0.90 (3H, m, NH—CH2-CH2-CH3), 1.40-1.50 (2H, m, —NH—CH2-CH2-CH3), 2.45-2.55 (2H, m, —NH—CH2-CH2-CH3), 3.55-3.65 (2H, s, Ar—CH2-N), 5.80-5.90 (2H, s, O—CH2-O), 6.65-6.85 (3H, 2×m, 3× aromatic H).

EXAMPLE 1.4: N-PIPERONYL ISOPROPYLAMINE

A mixture of benzo[d][1,3]dioxol-5-ylmethanamine (8 g, 52.9 mmol) and acetone (20 g, 344 mmol) was stirred at reflux until all starting amine had disappeared as monitored by GC analysis. The excess of acetone was removed by evaporation under reduced pressure. The residual oil was taken in 30 ml of methanol and placed in a 200 ml autoclave. Palladium 10% on carbon (1 g) was added and then the autoclave was pressurized with 3 bar of hydrogen. The mixture was stirred at ambient temperature until no more hydrogen was consumed. The reaction mixture was filtered to remove the catalyst. The filtrate was evaporated in vacuo. The residual brownish oil was purified by silica gel column chromatography using dichloromethane and heptane as eluent affording the title compound (6.5 g; yield 80%) as a slightly yellow oil.

$^1$H-NMR in CDCl3: 1.05-1.10 (6H, d, 2×—CH—CH3), 2.70-2.9 (1H, m, N—CH—), 3.60-3.70 (2H, s, Ar—CH2-N), 5.85-5.95 (2H, s, O—CH2-O), 6.65-6.85 (3H, 2×m, 3× aromatic H).

EXAMPLE 1.5: N-PIPERONYL 3-PENTYLAMINE

In a 250 ml round-bottomed flask was added benzo[d][1,3]dioxol-5-ylmethanamine (7 g, 46.3 mmol) to pentan-3-one (8 g, 93 mmol) in methanol (50 ml) to give a yellow solution. The mixture was stirred at reflux until all starting amine had disappeared as monitored by GC analysis. The solvent and the excess of 2-pentanone were removed under reduced pressure to give 10 g of the intermediate imine as a yellow-brown oil. In the next step, a 200 ml autoclave was charged with a mixture of the intermediate imine (8 g, 36.5 mmol) and Pd 10% on carbon (1 g) in methanol (30 ml).

The autoclave was pressurized with 3 bar of hydrogen and stirred at ambient temperature until no more hydrogen was consumed. The reaction mixture was filtered to remove the catalyst and methanol was evaporated in vacuo. The residual brownish oil was purified by vacuum distillation using a Kugelrohr apparatus affording 2.5 g of the title compound as a colourless oil (yield 31%, purity >98%).

$^1$H-NMR in CDCl3: 0.75-0.95 (6H, m, 2×—CH2-CH3), 1.30-1.55 (4H, m, 2×—CH2-CH3), 2.30-2.50 (1H, m, N—CH—), 3.60-3.70 (2H, s, Ar—CH2-N), 5.85-5.95 (2H, s, O—(CH2-O), 6.65-6.85 (3H, 2×m, 3× aromatic H).

EXAMPLE 1.6: N-PIPERONYL 2-HYDROXYETHYLAMINE

In a 250 mL round-bottomed flask was added 2-aminoethanol (8 g, 131 mmol) to a solution of benzo[d][1,3]dioxole-5-carbaldehyde (10 g, 66.6 mmol) in toluene (100 ml) to give a colourless solution. The mixture was stirred at reflux for 3 hrs. The formed water was removed by azeotropic distillation using a Dean stark apparatus. Then toluene was removed on rotary evaporator under reduced pressure. The excess of ethanolamine was removed by vacuum distillation. The remaining residual brownish oil was taken in 30 ml of methanol and placed in a 200 ml autoclave. Palladium 10% on carbon (1 g) was added and then the autoclave was pressurized with 5 bar of hydrogen. The mixture was stirred at ambient temperature until no more hydrogen was consumed. The reaction mixture was filtered to remove the catalyst and methanol was evaporated in vacuo. The residual brownish oil was purified by vacuum distillation using a Kugelrohr apparatus, affording 6.5 g of the title compound as a colourless viscous oil (bp 220-240° C./2-3 mbar). The oil solidified upon standing at room temperature (yield 91%, purity: >95%).

$^1$H-NMR in CDCl3: 2.65-2.75 (2H, m, N—CH2-CH2-OH), 3.55-3.65 (2H, m, N—CH2-CH2-OH), 3.60-3.70 (2H, s, Ar—CH2-N), 5.85-5.95 (2H, s, O—CH2-O), 6.65-6.85 (3H, 2×m, 3× aromatic H).

EXAMPLE 1.7: N-PIPERONYL 1,3-DIHYDROXY-2-PROPYLAMINE

A 250 ml autoclave was charged with 2-aminopropane-1,3-diol (3.03 g, 33.3 mmol), benzo[d][1,3]dioxole-5-carbaldehyde (5 g, 33.3 mmol) and 30 ml of methanol to give a colourless solution. The autoclave was closed and stirred at room temperature for 3 hrs. Then 0.5 g of palladium 10% on carbon was added. Then the autoclave was pressurized with 5 bar of hydrogen and stirred at ambient temperature until no more hydrogen was consumed. The reaction mixture was filtered to remove the catalyst. The filtrate was evaporated to afford 7.2 g of pure title compound as white crystals (yield 96%).

$^1$H-NMR in DMSO-d6: 2.40-2.55 (1H, m, NH—CH—), 3.25-3.45 (4H, 2×m, 2×—CH2-OH), 3.60-3.70 (2H, s, Ar—CH2-N), 5.85-5.95 (2H, s, O—CH2-O), 6.70-6.95 (3H, s and 2×m, 3× aromatic H).

EXAMPLE 1.8: N-PIPERONYL ALANINE

In a 250 ml autoclave was added benzo[d][1,3]dioxole-5-carbaldehyde (4.89 g, 32.6 mmol) to a mixture of alanine ethyl ester hydrochloride (5 g, 32.6 mmol) and triethylamine (4.54 ml, 32.6 mmol) in methanol (30 ml). The autoclave was closed and stirred at 60° C. for 3 hrs. After the mixture was cooled to room temperature, 0.5 g of palladium 10% on carbon was added and then stirred at ambient temperature under 3 bar hydrogen for 3 hours. The reaction mixture was filtered to remove the catalyst. The filtrate was concentrated to dryness to yield 7.5 g of crude N-piperonyl-alanine ethyl ester.

In the next step, a solution of N-piperonyl-alanine ethyl ester (6 g, 23.88 mmol) in methanol (10 ml) was added to 5% aqueous sodium hydroxide (38.2 g, 47.8 mmol) to give a yellow solution. After 3 hours stirring, the solution was neutralized with 5% HCl. Then 100 ml of ether was added to the solution and stirred for 15 minutes at room temperature. The formed white crystals were filtered, washed with water and ether and then dried in vacuum oven at 50° C. affording 4.5 g of the title compound (yield 84%, purity >95%).

$^1$H-NMR in DMSO-d6: 1.40-1.50 (3H, d, NH—CH—CH3), 3.80-3.90 (1H, m, NH—CH—CH3COOH), 3.9-4.1 (2H, s, Ar—CH2-NH—), 5.85-5.95 (2H, s, O—CH2-O), 6.70-6.95 (3H, s and 2×m, 3× aromatic H).

EXAMPLE 1.9: N-VANILLYL ETHYLAMINE HYDROCHLORIDE

A 250 ml autoclave was charged with 100 ml of ethylamine 2M in methanol (81 g, 200 mmol) and 4-hydroxy-3-methoxybenzaldehyde (7 g, 46.0 mmol) to give a colourless solution. The autoclave was closed and stirred at 35° C. for 2 hrs. Then 0.9 g of palladium 10% on carbon was added and stirred at ambient temperature under 5 bar of hydrogen until no more hydrogen was consumed. The reaction mixture was filtered to remove the catalyst. The filtrate was evaporated to furnish a brownish thick oil, which was dissolved in 20 ml of methanol and then acidified with 1.5M HCl in methanol. To the solution was added 200 ml of diethyl ether and stirred until complete precipitation was achieved. The white precipitate was filtered, washed with ether and then dried in vacuum oven at 35° C. affording 7.9 g of the title compound (yield 75%, purity >95%).

$^1$H-NMR in DMSO-d6: 1.15-1.25 (3H, m, NH—CH2-CH3), 2.70-2.95 (2H, m, —NH—CH2-CH3), 3.7-3.85 (3H, s, Ar—O—CH3), 3.90-4.10 (2H, m, Ar—CH2-N), 6.65-6.25 (2H, 2×m, 2× aromatic H), 7.25-7.35 (1H, s, aromatic H).

EXAMPLE 1.10: N-(2-HYDROXYETHYL) VANILLYLAMINE HYDROCHLORIDE

A 250 ml autoclave was charged with a mixture of 4-hydroxy-3-methoxybenzaldehyde (5 g, 32.9 mmol) and 2-aminoethanol (2.208 g, 36.1 mmol) in methanol (30 ml) and stirred at room temperature for 2 hrs. Then 0.5 g of palladium 10% on carbon was added and stirred at ambient temperature under 3 bar of hydrogen until no more hydrogen was consumed. The reaction mixture was filtered to remove the catalyst. The filtrate was evaporated to furnish a brownish thick oil, which was dissolved in 20 ml of methanol and then acidified with 1.5M HCl in methanol. To the solution was added diethyl ether until complete precipitation was achieved. The white precipitate was filtered, washed with ether and then dried in vacuum oven at 35° C. affording 4.9 g of the title compound (yield 61%, purity >95%).

$^1$H-NMR in DMSO-d6: 2.75-2.95 (2H, m, N—CH2-CH2-OH), 3.60-3.75 (2H, m, N—CH2-CH2-OH), 3.75-3.80 (3H, s, Ar—O—CH3), 3.95-4.10 (2H, m, Ar—CH2-N), 6.65-7.25 (2H, 2×m, 2× aromatic H), 7.25-7.35 (1H, s, aromatic H).

EXAMPLE 2: TASTING OF NaCl SOLUTIONS

An aqueous NaCl solution (0.5% by weight) was prepared (reference) to which 5 ppm of a compound of formula (I) was added.

The samples were tasted by a group of flavourists. The intensity of the umami and salt taste of the NaCl solutions comprising a compound of formula (I) (0.5% NaCl; 5 ppm of a compound of formula (I)) was compared with that of the reference (0.5% NaCl) and rated according to the following intensity scale:

Taste effect much lower than reference: −3

Taste effect lower than reference: −2

Taste effect slightly lower than reference: −1

Taste effect same as reference: 0

Taste effect slightly higher than reference: 1

Taste effect higher than reference: 2

Taste effect much higher than reference: 3

The results (average of ratings given by the individual flavourists) are shown in Table 1 below.

TABLE 1

| | Taste intensity | |
|---|---|---|
| Sample | Umami | Salt (NaCl) |
| 0.5% NaCl (reference) | 0.00 | 0.00 |
| N-piperonyl 3-pentylamine | 0.00 | 0.50 |
| N-piperonyl ethylamine | 0.25 | 0.75 |
| N-piperonyl isopropylamine | 0.00 | 0.50 |
| N-piperonyl 2-hydroxyethylamine | 0.00 | 0.75 |
| N-piperonyl 1,3-dihydroxy-2-propylamine | 0.50 | 1.00 |
| N-piperonyl alanine | 0.00 | 0.50 |
| N-vanillyl ethylamine hydrochloride | 0.67 | 0.67 |
| N-piperonyl 1-hydroxy-2-butylamine* | 0.33 | 0.67 |
| N-(2-hydroxyethyl) vanillylamine hydrochloride | 0.67 | 0.33 |
| N-piperonyl methylamine | 0.00 | 0.25 |
| N-piperonyl n-propylamine | 0.00 | 1.00 |

*Purchased from ChemBridge, product number 7961435

EXAMPLE 3: TASTE ENHANCEMENT

Six solutions were prepared:

A a solution of 0.5% NaCl

B a solution of 0.5% NaCl and 0.03% MSG (monosodium glutamate)

C a solution of 0.5% NaCl and 0.015% Ribo (disodium 5-ribonucleotides=E635)

D a solution of 0.5% NaCl and 5 ppm of a compound of formula (I)

E a solution of 0.5% NaCl and 0.03% MSG and 5 ppm a compound of formula (I)

F a solution of 0.5% NaCl and 0.015% Ribo and 5 ppm of a compound of formula (I)

The samples were tasted by a group of 5-10 flavourists aged between 30 and 60. The taste of solution D was compared with that of A to determine the enhancement effect of a compound of formula (I) on NaCl. Similarly, solution E was compared with solution B and solution F with solution C to determine the enhancement effect of a compound of formula (I) on MSG and Ribo respectively. The effect was marked on a linear scale between 0 and 10, the greater the value the greater the effect. For a reference, the taste solutions of B and C were compared with A as well. The results are summarized in Table 2, below.

TABLE 2

| | Taste intensity | | |
|---|---|---|---|
| Sample | NaCl | MSG | Ribo |
| solution A (salt reference) | 0.0 | — | — |
| solution B (MSG reference) | — | 5.0 | — |
| solution C (Ribo reference) | — | — | 5.0 |
| N-piperonyl ethylamine | 1.3 | 6.6 | 5.6 |
| N-piperonyl 1,3-dihydroxy-2-propylamine | 2.3 | 5.0 | 5.0 |
| N-piperonyl 3-pentylamine | 1.0 | 6.3 | 5.3 |
| N-piperonyl 1-hydroxy-2-butylamine | 1.0 | 5.3 | 5.0 |

As can be seen from the results above, the addition of compounds of formula (I) to a solution having umami- and/or salt taste imparts the intensity of umami- and/or salt taste.

EXAMPLE 4: BOUILLON

A vegetarian bouillon mix was prepared from 204.71 g of sodium chloride, 147.76 g of dextrose monohydrate (ex Tapioca), 0.19 g of celery oleoresin, 0.19 g of oleoresin coriander seed, 418.64 g maltodextrin 5-8 DE, 37.65 g vegetable oil soya bean refined, 28.24 g yeast standard light, 3.76 g of onion powder, 3.76 g of garlic powder, 0.47 g of white pepper and 154.35 g of potato starch.

32 g of the well-mixed ingredients was added to 1 L of boiling water and stirred until completely dissolved.

A small group of flavourists (2 male, 2 female) compared the taste of the reference bouillon with that of the following bouillons:

A a batch of the same bouillon containing 10 ppm of N-piperonyl ethylamine: The flavourists agreed that the test bouillon was more umami, more salty, slightly sweeter and had a slightly more powdery volatile effect than the reference bouillon.

B a batch of the same bouillon containing 10 ppm of N-piperonyl 3-pentylamine: The flavourists agreed that the test bouillon was more umami, sweeter and more lingering than the reference bouillon.

EXAMPLE 5: BREAD

A bread flour mixture was prepared by mixing 1250 g of wheat flour, 250 g of white wheat flour and 60 g of yeast. Two salt mixtures were added to separate flour mixtures:

A 20 g of NaCl

B 20 g of NaCl and 0.02 g N-piperonyl ethylamine

Doughs were prepared by mixing the ingredients and adding 900 g of water. The doughs were allowed to rise at room temperature for 2 hours and baked at 220° C. for 45 minutes.

A panel of professional tasters compared the breads. The bread B was unanimously preferred over reference bread A.

The invention claimed is:

1. A comestible composition comprising a compound selected from the group consisting N-piperonyl methylamine, N-piperonyl ethylamine, N-piperonyl n-propylamine, N-piperonyl isopropylamine, N-piperonyl 3-pentylamine, N-piperonyl 2-hydroxyethylamine, N-piperonyl 1,3-dihydroxy-2-propylamine, N-piperonyl alanine, N-vanillyl ethylamine hydrochloride, and N-(2-hydroxyethyl) vanillylamine hydrochloride, a comestibly acceptable salt thereof, or mixtures thereof.

2. The comestible composition according to claim 1 wherein the compound is present in an amount of 1 to 2500 ppm.

3. The comestible composition according to claim 1 comprising monosodium glutamate (MSG) or salt (NaCl).

4. The comestible composition according to claim 3 wherein the monosodium glutamate (MSG) is present in amounts of about 100 to about 500 ppm.

5. The comestible composition according to claim 3 wherein the salt (NaCl) is present in amounts of about 0.4% to about 2 weight %.

6. The comestible composition according to claim 1 selected from food products and beverages.

7. A comestible composition comprising a compound selected from the group consisting N-piperonyl methylamine, N-piperonyl ethylamine, N-piperonyl n-propylamine, N-piperonyl isopropylamine, N-piperonyl 3-pentylamine, N-piperonyl 2-hydroxyethylamine, N-piperonyl 1,3-dihydroxy-2-propylamine, N-piperonyl alanine, N-vanillyl ethylamine hydrochloride, and N-(2-hydroxyethyl) vanillylamine hydrochloride a comestibly acceptable salt thereof, or mixtures thereof, to impart, enhance, or modify an umami- and/or salt-taste in the comestible composition.

8. A method of imparting, enhancing or modifying an umami- and/or salt-taste in a comestible product comprising the steps of:
   a) providing at least one comestible product, and
   b) combining the comestible product with a compound selected from the group consisting N-piperonyl methylamine, N-piperonyl ethylamine, N-piperonyl n-propylamine, N-piperonyl isopropylamine, N-piperonyl 3-pentylamine, N-piperonyl 2-hydroxyethylamine, N-piperonyl 1,3-dihydroxy-2-propylamine, N-piperonyl alanine, N-vanillyl ethylamine hydrochloride, and N-(2-hydroxyethyl) vanillylamine hydrochloride or a comestibly acceptable salt thereof, so as to form a modified comestible product comprising at least about 1 ppm of the compound of formula (I).

9. The comestible composition according to claim 2, comprising monosodium glutamate (MSG) or salt (NaCl).

* * * * *